United States Patent [19]

Jones et al.

[11] Patent Number: 4,495,374
[45] Date of Patent: Jan. 22, 1985

[54] METHANE CONVERSION

[75] Inventors: C. A. Jones, Newtown Square; John A. Sofranko, West Chester, both of Pa.

[73] Assignee: Atlantic Richfield Company, Los Angeles, Calif.

[21] Appl. No.: 522,936

[22] Filed: Aug. 12, 1983

[51] Int. Cl.³ .............................................. C07C 2/00
[52] U.S. Cl. .................................. 585/500; 585/400; 585/417; 585/541; 585/654; 585/658; 585/700; 585/943; 502/208
[58] Field of Search .............. 585/500, 541, 654, 658, 585/700, 400, 417, 943

[56] References Cited

U.S. PATENT DOCUMENTS

| | | | |
|---|---|---|---|
| 1,995,136 | 3/1935 | Winkler et al. | 585/500 |
| 2,216,130 | 10/1940 | Pier et al. | 585/943 |
| 2,326,799 | 8/1943 | Piere et al. | 585/700 |
| 2,608,534 | 8/1952 | Fleck | 585/654 |
| 3,900,525 | 8/1975 | Christmann et al. | 585/541 |
| 4,066,704 | 1/1978 | Harns et al. | 585/500 |
| 4,205,194 | 5/1980 | Mitchell et al. | 585/500 |
| 4,239,658 | 12/1980 | Mitchell et al. | 585/500 |

FOREIGN PATENT DOCUMENTS

| | | | |
|---|---|---|---|
| 258608 | 1/1928 | United Kingdom | 585/943 |
| 255829 | 5/1976 | United Kingdom | 585/700 |

OTHER PUBLICATIONS

Keller, G. E., "Synthesis of Ethylene via Oxidative Coupling of Methane", J. of Catalysis, 73 9-19, 1982.

Primary Examiner—Delbert E. Gantz
Assistant Examiner—Cynthia A. Prezlock
Attorney, Agent, or Firm—Craig E. Larson

[57] ABSTRACT

An improved method for converting methane to higher hydrocarbon products by contacting a gas comprising methane and an oxidative synthesizing agent under systhesis conditions, the improvement which comprises contacting methane with an oxidative synthesizing agent containing a promoting amount of alkaline earth metal and/or compounds thereof. Magnesium is a particularly effective promoter. Stability of the promoted contact agent is enhanced by the presence of phosphorus.

26 Claims, No Drawings

4,495,374

METHANE CONVERSION

BACKGROUND OF THE INVENTION

1. Field of the Invention

This invention relates to synthesis of hydrocarbons from a methane source. A particular application of this invention is a method for converting natural gas to a more readily transportable material.

2. Description of the Prior Art

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_{3}+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion to olefins such as ethylene or propylene would be extremely valuable to the chemical industry.

Recently, it has been discovered that methane may be converted to higher hydrocarbons by a process which comprises contacting methane and an oxidative synthesizing agent at synthesizing conditions (e.g., at a temperature selected within the of from about 500° to about 1000° C.). Oxidative synthesizing agents are compositions having as a principal component at least one oxide of at least one metal which compositions produce $C_{2}+$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony and bismuth are most useful. See commonly-assigned U.S. patent application Ser. Nos. 522,925 (filed Aug. 12, 1983, now U.S. Pat. No. 4,443,649), 522,944 (filed Aug. 12, 1983, now U.S. Pat. No. 4,444,984), 522,942 (filed Aug. 12, 1983, now U.S. Pat. No. 4,443,648), 522,905 (filed Aug. 12, 1983, now U.S. Pat. No. 4,443,645), 522,877 (filed Aug. 12, 1983, now U.S. Pat. No. 4,443,647), 522,876 (filed Aug. 12, 1983, now U.S. Pat. No. 4,443,644), and 522,906 (filed Aug. 12, 1983, now U.S. Pat. No. 4,443,646) contents of which are incorporated herein by reference.

Commonly-assigned U.S. patent application Ser. No. 06/522,935 discloses and claims a process which comprises contacting methane with an oxidative synthesizing agent under elevated pressure (2-100 atmospheres) to produce greater amounts of $C_{3}+$ hydrocarbon products.

Commonly-assigned U.S. patent application Ser. No. 06/522,938 discloses and claims a process for the conversion of methane to higher hydrocarbons which comprises contacting methane with particles comprising an oxidative synthesizing agent which particles recirculate between two physically separate zones—a methane contact zone and an oxygen contact zone.

As noted, the reaction products of such processes are mainly ethylene, ethane, other light hydrocarbons, carbon oxides, coke and water. It would be beneficial to these oxidative synthesis processes to reduce selectivities to carbon oxides and coke.

Accordingly, an object of this invention is to provide an improved process for converting methane to higher hydrocarbons. A further object of this invention is an improved oxidative synthesizing agent, one capable of converting methane with reduced by-product selectivities. A still further object of this invention is an oxidative synthesizing agent with improved stability, an agent that maintains desirable conversion properties for longer periods of time.

Other aspects, objects and the several advantages of this invention will become apparent to those skilled in the art upon reading this disclosure and the appended claims.

SUMMARY OF THE INVENTION

It has now been found that the conversion of methane to higher hydrocarbons is improved by contacting a gas comprising methane at synthesizing conditions with a promoted oxidative synthesizing agent which comprises:

(a) at least one reducible oxide of at least one metal selected from the group consisting of Mn, Sn, In, Ge, Pb, Sb and Bi and (b) at least one promoter selected from the group consisting of alkaline earth metals and compounds thereof.

Alkaline earth metals are selected from the group consisting of Mg, Ca, Sr and Ba. Preferred promoters are Mg and Ca. Magnesium is a particularly preferred promoter. Particularly preferred reducible metal oxides are reducible oxides of manganese.

In a separate, distinct embodiment of the present invention, it has been found that the stability of the promoted oxidative synthesizing agent is enhanced by incorporating a stabilizing amount of phosphorus into the composition.

The present process is distinguished from previously known pyrolytic methane conversion processes by the use of the aforementioned reducible oxides to synthesize higher hydrocarbons from methane with coproduction of water, rather than hydrogen.

The present process is distinguished from previously suggested methane conversion processes which rely primarily on interactions between methane and at least one of nickel and the noble metals, such as rhodium, palladium, silver, osmium, iridium, platinum and gold.

An example of this type of process is disclosed in U.S. Pat. No. 4,205,194. The present process does not require that methane be contacted with one or more of nickel and such noble metals and compounds thereof.

Moreover, in a preferred embodiment, such contacting is carried out in the substantial absence of catalytically effective nickel and the noble metals and compounds thereof to minimize the deleterious catalytic effects of such metals and compounds thereof. For example, at the conditions, e.g., temperatures, useful for the contacting step of the present invention, these metals when contacted with methane tend to promote coke formation, and the metal oxides when contacted with methane tend to promote formation of combustion products ($CO_x$) rather than the desired hydrocarbons. The term "catalytically effective" is used herein to identify that quantity of one or more of nickel and the noble metals and compounds thereof which when present substantially changes the distribution of products obtained in the contacting step of this invention relative to such contacting in the absence of such metals and compounds thereof.

DETAILED DESCRIPTION OF THE INVENTION

Oxidative synthesizing agents comprise at least one oxide of at least one metal, which oxides when contacted with methane at synthesizing conditions (e.g., at a temperature selected within the range of about 500° to 1000° C.) produce higher hydrocarbon products, co-product water, and a reduced metal oxide. The composition thus contains at least one reducible oxide of at least one metal. The term "reducible" is used to identify those oxides of metals which are reduced by contacting methane at synthesizing conditions (e.g., at temperatures selected within the range of about 500°-1000° C.). The term "oxide(s) of metal(s)" includes: (1) one or more metal oxides (i.e., compounds described by the general formula $M_xO_y$ wherein M is a metal and the subscripts $x$ and $y$ designate the relative atomic proportions of metal and oxygen in the composition) and/or (2) one or more oxygen-containing metal compounds, provided that such oxides and compounds have the capability of performing to produce higher hydrocarbon products as set forth herein.

Preferred oxidative synthesizing agents comprise reducible oxides of metals selected from the group consisting of Mn, Sn, In, Ge, Sb, Pb, and Bi and mixtures thereof. Particularly preferred oxidative synthesizing agents comprise a reducible oxide of manganese and mixtures of a reducible oxide of manganese with other oxidative synthesizing agents.

The promoted oxidative synthesizing agent of this invention contains, in addition to the foregoing elements, at least one alkaline earth metal. The atomic ratio in which these materials are combined to form the synthesizing agent is not narrowly critical. However, the preferred atomic ratio of the reducible oxide component (expressed as the metal, e.g., Mn) to the alkaline earth component (expressed as the metal, e.g., Mg) is within the range of about 0.01–100:1, more preferably within the range of about 0.1–10:1.

The promoted oxidative synthesizing agent may also contain at least one phosphorus component in a distinct, preferred embodiment. The amount of the phosphorus component contained in the synthesizing agent is again not narrowly critical. The atomic ratio of phosphorus to the reducible oxide component (e.g., Mn) is preferably less than about 10:1. More preferably this ratio is within the range of about 0.1–0.5:1.

A preferred oxidative synthesizing agent used in the process of this invention may be further expressed by the following empirical formula:

$$A_a B_b P_c O_d$$

wherein A is selected from the group consisting of Mn, Sn, In, Ge, Pb, Sb, Bi and mixtures thereof; B is selected from the group consisting of alkaline earth metals and mixtures thereof; a to d indicate the atomic ratio of each component; and when a is 10, b is within the range of about 1–100, c is within the range of about 0–100, and d has a value which is determined by the valence and proportions of the other elements present. These components may be associated with a support material as described below.

The promoted oxidative synthesizing agent may be supported by or diluted with conventional support materials such as silica, alumina, titania, zirconia and the like, and combinations thereof. Moreover, the support material may comprise the alkaline earth promoter itself (e.g., suitable supports include MgO, CaO, BaO, etc.).

The promoted oxidative synthesizing agent can be prepared by any suitable method. Conventional methods such as precipitation, co-precipitation, impregnation, or dry-mixing can be used. Supported solids may be prepared by methods such as adsorption, impregnation, precipitation, co-precipitation, and dry-mixing. Thus, a compound of Mn, Sn, In, Ge, Pb, Sb and/or Bi; a compound of an alkaline earth metal; and optionally a compound of phosphorus can be combined in any suitable way. When phosphorus is incorporated in the agent, it is desirable to provide it in the form of a phosphate of an alkaline earth metal. Substantially any compound of these elements can be employed in the preparation of the promoted synthesizing agent.

A suitable method of preparation is to impregnate a support with solutions of compounds of the desired metals. Compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried in an oven to remove solvent and the dried solid is prepared for use by calcining, preferably in air at a temperature selected within the range of about 300° to 1200° C. Particular calcination temperatures will vary depending upon the particular metal compound or compounds employed.

If phosphorus is used, the alkaline earth metal and phosphorus are preferably added to the composition as compounds containing both P and alkaline earth metals. Examples are the orthophosphates, metaphosphates, and pyrophosphates of alkaline earth metals. Pyrophosphates have been found to give desirable results. The alkaline earth metal and the phosphorus can be incorporated into the synthesizing agent as separate compounds. Suitable phosphorus compounds useful for preparing the compositions include orthophosphoric acid, ammonium phosphates and ammonium hydrogenphosphates.

Regardless of how the components of the synthesizing agent are combined, the resulting composite generally will be dried and calcined at elevated temperatures in an oxygen-containing gas (e.g., air) prior to use in the process of this invention.

In addition to methane, the feedstock employed in the method of this invention may contain other hydrocarbon or non-hydrocarbon components, although the methane content should typically be within the range of about 40 to 100 volume percent, preferably from about 80 to 100 volume percent, more preferably from about 90 to 100 volume percent.

Operating temperatures for the contacting of methane-containing gas and the promoted oxidative synthesizing agent are selected within the range of about 500 to 1000° C., the particular temperature selected depending upon the particular reducible metal oxide(s) employed in the promoted oxidative synthesizing agent. For example, reducible oxides of certain metals, may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a promoted oxidative synthesizing agent to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting reduced compositions with oxygen (e.g., an oxygen-containing gas such as air) at a temperature selected within the range of about 300° to 1200° C., the particular temperature selected depending on the metal(s) included in the oxidative synthesizing agent.

In carrying out the present process, a single reactor apparatus containing a fixed bed of solids may be used with intermittent or pulsed flow of a first gas comprising methane and a second gas comprising oxygen (e.g., oxygen, oxygen diluted with an inert gas, or air, preferably air). The methane contacting step and the oxygen contacting step are more preferably performed in physically separate zones with solids recirculating between the two zones.

Thus, a suitable method for synthesizing hydrocarbons from a methane source comprises: (a) contacting a gas comprising methane and particles comprising a promoted oxidative synthesizing agent to form higher hydrocarbon products, co-product water, and reduced metal oxide; (b) removing particles comprising reduced synthesizing agent from the first zone and contacting the reduced particles in a second zone with an oxygen-containing gas to form particles comprising a promoted oxidative synthesizing agent; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

Particles comprising a promoted oxidative synthesizing agent which are contacted with methane may be maintained as fluidized, ebullating, or entrained beds of solids. Preferably methane is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In the more preferred embodiment of the present invention, methane feedstock and particles comprising a promoted oxidative synthesizing agent are continuously introduced into a methane contact zone maintained at synthesizing conditions. Synthesizing conditions include the temperatures and pressures described above. Gaseous reaction products from the methane contact zone (separated from entrained solids) are further processed—e.g., they are passed through a fractionating system wherein the desired hydrocarbon products are separated from unconverted methane and combustion products. Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising a promoted oxidative synthesizing agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of synthesizing system.

The invention is further illustrated by reference to the following examples.

Methane-contact runs were made at about atmospheric pressure in quartz tube reactors (12 mm. inside diameter) packed with 7 ml. of catalyst. The reactors were brought up to temperature under a flow of nitrogen which was switched to methane at the start of the run. Unless otherwise indicated, all methane.contact runs described in the following examples had a duration of 2 minutes. At the end of each methane-contact run, the reactor was flushed with nitrogen and the solids were regenerated under a flow of air (usually at 800° C. for 30 minutes). The reactor was then again flushed with nitrogen and the cycle repeated. The results reported below are based on the cumulative sample collected after the contact solid has "equilibrated"—i.e., after the aberrant characteristics of the fresh solid have dissipated. This has been done to allow more meaningful comparisons to be made between the various contact agents within the scope of this invention and further comparisons between contact agents within the scope of this invention and other contact agents. Three to six cycles of methane-contact and regeneration are generally sufficient to equilibrate the solids.

Experimental results reported below include conversions and selectivities calculated on a carbon mole basis.

Space velocities are reported as gas hourly space velocities (hr.$^{-1}$) and are identified as "GHSV" in the Examples.

EXAMPLE 1-3 AND COMPARATIVE EXAMPLE A

Supported manganese oxides promoted by various alkaline earth metals were made by impregnating a silica support with the appropriate amount of manganese (as manganese acetate) and the appropriate amount of alkaline earth metal (also as the acetate) from water solutions. The support was Houdry HSC 534 silica. The impregnated solids were dried at 110° C. for 4 hours and then calcined in air at 700° C. for 16 hours. All calcined solids contained 10 wt. % Mn and each contained the same mole % of alkaline earth metal. Results reported below in Table I are based on analyses of cumulative samples collected during the third, two-minute, methane-contact run for each promoted oxidative synthesizing agent. Run conditions were 800° C. and 860 GHSV. Table I also shows results obtained over an unpromoted oxidative synthesizing agent.

TABLE I

| Example | Oxidative Synthesizing Agent | % CH$_4$ Conversion | % C$_{2-7}$ Selectivity |
| --- | --- | --- | --- |
| 1 | 10% Ba/10% Mn/SiO$_2$ | 13.4 | 65 |
| 2 | 3.0% Ca/10% Mn/SiO$_2$ | 3.1 | 76 |
| 3 | 1.8% Mg/10% Mn/SiO$_2$ | 8.6 | 67 |
| A | 10% Mn/SiO$_2$ | 7.6 | 56 |

1. In an improved method for converting methane to higher hydrocarbon products which comprises contacting a gas comprising methane at synthesizing conditions with at least one reducible oxide of at least one metal which oxides when contacted with methane at synthesizing conditions are reduced and produce higher hydrocarbon products and water, said contacting being carried out in the substantial absence of catalytically effective Ni, Rh, Pd, Ag, Os, Ir, Pt, Au and mixtures thereof, the improvement which comprises conducting the contacting in the presence of a promoting amount of at least one promoter selected from the group consisting of alkaline earth metals and compounds thereof.

2. A method for converting methane to higher hydrocarbon products which comprises contacting a gas comprising methane at synthesizing conditions with a promoted oxidative synthesizing agent which agent comprises:
  (a) at least one reducible oxide of at least one metal selected from the group consisting of Mn, Sn, In, Ge, Pb, Sb and Bi and
  (b) a promoting amount of at least one promoter selected from the group consisting of alkaline earth metals and compounds thereof,
provided that when said oxidative synthesizing agent comprises a reducible oxide of manganese or indium, said contacting is carried out in the substantial absence of catalytically effective Ni, Rh, Pd, Ag, Os, Ir, Pt, Au and compounds thereof.

3. The method of claim 2 wherein the gas comprising methane contains from about 40 to about 100 volume percent methane.

4. The method of claim 2 wherein the gas comprising methane contains from about 80 to about 100 volume percent methane.

5. The method of claim 2 wherein the gas comprising methane contains from about 90 to about 100 volume percent methane.

6. The method of claim 2 wherein the gas comprising methane is natural gas.

7. The method of claim 2 wherein the gas comprising methane is processed natural gas.

8. The method of claim 2 wherein the promoter is selected from the group consisting of Mg, Ca, Sr, Ba, and compounds thereof.

9. The method of claim 2 wherein the promoter is selected from the group consisting of magnesium, magnesium compounds and mixtures thereof.

10. The method of claim 2 wherein the promoter is selected from the group consisting of calcium, calcium compounds and mixtures thereof.

11. The method of claim 2 wherein the said reducible oxide and the said promoter are associated with a support material.

12. The method of claim 11 wherein the support material is silica.

13. The method of claim 11 wherein the support material comprises the said promoter.

14. The method of claim 13 wherein the support material comprises MgO.

15. The method of claim 13 wherein the support material comprises CaO.

16. The method of claim 2 wherein the oxidative synthesizing agent further comprises a stabilizing amount of phosphorus.

17. The method of claim 2 wherein the promoted oxidative synthesizing agent is described by the empirical formula:

$$A_aB_bP_cO_d$$

wherein A is selected from the group consisting of Mn, Sn, In, Ge, Pb, Sb, Bi and mixtures thereof; B is selected from the group consisting of Mg, Ca, Sr, Ba and mixtures thereof; a, b, c, and d indicate the atomic ratio of each component; and when a is 10, b is within the range of about 1-100, c is within the range of about 0-100, and d has a value which is determined by the valence and proportion of the other elements present.

18. The method of claim 17 wherein A is Mn.

19. The method of claim 18 wherein B is Mg.

20. The method of claim 18 wherein B is Ca.

21. The method of claim 2 wherein said contacting is carried out at a temperature selected within the range of about 500° to 1000° C.

22. A method for synthesizing hydrocarbons from a methane source which comprises:
  (a) contacting a gas comprising methane with a promoted oxidative synthesizing agent comprising at least one reducible oxide of at least one metal selected from the group consisting of Mn, Sn, In, Ge, Pb, Sb, and Bi and a promoting amount of at least one promoter selected from the group consisting of alkaline earth metals and compounds thereof at synthesizing conditions in a first zone to form higher hydrocarbons, co-product water, and solids comprising reduced metal oxide, provided that when said promoted oxidative synthesizing agent comprises a reducible oxide of manganese or indium, said contacting is carried out in the substantial absence of catalytically effective Ni, Rh, Pd, Ag, Os, Ir, Pt, Au and compounds thereof,
(b) recovering higher hydrocarbons,
(c) at least periodically contacting solids comprising reduced metal oxide with an oxygen-containing gas in a second zone to produce a promoted oxidative synthesizing agent; and
(d) returning said promoted oxidative synthesizing agent formed in the second zone to the first zone.

23. The method of claim 22 wherein said reducible oxide is a reducible oxide of Mn.

24. The method of claim 22 wherein the promoter is selected from the group consisting of magnesium, magnesium compounds, and mixtures thereof.

25. The method of claim 22 wherein the promoter is selected from the group consisting of calcium, calcium compounds, and mixtures thereof.

26. The method of claim 22 wherein a gas comprising methane is contacted with said promoted oxidative synthesizing agent at a temperature selected within the range of about 500° to 1000° C.

* * * * *